(12) United States Patent
Mech et al.

(10) Patent No.: US 7,127,286 B2
(45) Date of Patent: Oct. 24, 2006

(54) IMPLANTABLE DEVICE USING ULTRA-NANOCRYSTALLINE DIAMOND

(75) Inventors: Brian V. Mech, Sherman Oaks, CA (US); Robert J. Greenberg, Los Angeles, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 122 days.

(21) Appl. No.: 10/039,842

(22) Filed: Oct. 26, 2001

(65) Prior Publication Data
US 2002/0120296 A1 Aug. 29, 2002

Related U.S. Application Data

(60) Provisional application No. 60/272,962, filed on Feb. 28, 2001.

(51) Int. Cl.
*A61N 1/00* (2006.01)
*A61N 1/08* (2006.01)
*A61N 5/00* (2006.01)

(52) U.S. Cl. .............................. 607/2; 607/53; 600/300

(58) Field of Classification Search .................... 607/1, 607/2, 36; 604/891.1; 427/2.1, 2.11, 2.24, 427/2.12; 600/300, 347, 365, 373
See application file for complete search history.

(56) References Cited

U.S. PATENT DOCUMENTS

| 4,991,582 | A | 2/1991 | Byers et al. |
| 5,660,163 | A | 8/1997 | Schulman et al. |
| 5,750,926 | A | 5/1998 | Schulman et al. |
| 5,999,848 | A | 12/1999 | Gord et al. |
| 6,043,437 | A | 3/2000 | Schulman et al. |
| 6,081,736 | A | 6/2000 | Colvin et al. |
| 6,119,028 | A | 9/2000 | Schulman et al. |
| 6,410,877 | B1 | 6/2002 | Dixon et al. |

OTHER PUBLICATIONS

D.M. Gruen, et al. "Buckyball Microwave Plasmas: Fragmentation and Diamond Film Growth", J. Appl. Phys., 75 (3) 1758-63 (1994).
D.M. Gruen, "Nanocrystalline Diamond Films" Annu. Rev. Mater. Sci., 29 211-59 (1999).

*Primary Examiner*—Mark Bockelman
(74) *Attorney, Agent, or Firm*—Scott B. Dunbar; Tomas Lendvai

(57) ABSTRACT

An implantable biocompatible device, that may be either a sensor or stimulator, having electronic circuitry and electrodes formed on a substrate, is uniformly covered with a coating approximately one-micron thick of ultra-nanocrystalline diamond, hermetically sealing the electronic circuitry. Selected electrodes are either left uncovered during coating or uncovered by conventional patterning techniques, allowing the electrodes to be exposed to living tissue and fluids. The ultra-nanocrystalline diamond coating may be doped to create electrically conductive electrodes. These approaches eliminate the need for a hermetically sealed lid or cover to protect hybrid electronic circuitry, and thus allow the device to be thinner than otherwise possible. The conformal ultra-nanocrystalline diamond coating uniformly covers the device, providing relief from sharp edges and producing a strong, uniformly thick hermetic coating around sharp edges and on high aspect-ratio parts.

8 Claims, 1 Drawing Sheet

US 7,127,286 B2

IMPLANTABLE DEVICE USING ULTRA-NANOCRYSTALLINE DIAMOND

CROSS REFERENCE TO RELATED APPLICATIONS

This application claims the benefit of U.S. Provisional application No. 60/272,962, filed Feb. 28, 2001. This application is related to U.S. patent application, Implantable Microfluidic Delivery System Using Ultra-Nanocrystalline Diamond Coating, Ser. No. 10/046,458, filed on even date herewith and incorporated herein by reference.

FEDERALLY SPONSORED RESEARCH

This invention was made with government support under grant No. R24EY12893-01, awarded by the National Institutes of Health. The government has certain rights in the invention.

FIELD OF THE INVENTION

The present invention relates to an implantable device that communicates with living tissue, wherein electronic circuitry associated with the implantable device is coated with a thin film that is biocompatible and hermetic.

BACKGROUND OF THE INVENTION

Hermetic electrically insulating materials are desirable for packaging of electronics in implantable stimulating and sensing devices, where implantation is in living tissue in a living body. The implanted devices must be biocompatible. The devices must not only exhibit the ability to resist the aggressive environment present in the body, but must also be compatible with both the living tissue and with the other materials of construction for the device itself. The materials are selected to avoid both galvanic and electrolytic corrosion. Typical materials of construction for implantable devices include ceramics, plastics, or metals. The ceramics may be glass, or a metal oxide, such as alumina, titania, zirconia, stabilized-zirconia, partially-stabilized zirconia, tetragonal zirconia, magnesia-stabilized zirconia, ceria-stabilized zirconia, yttria-stabilized zirconia, or calcia-stabilized zirconia, or yttria-stabilized zirconia, although other ceramic materials may also be used. The plastics may be epoxy, polycarbonate, or plexiglass. Typical metals include titanium or titanium alloy (such as Ti-6 Al-4 V), although other metals, such as platinum, iridium, platinum-iridium, stainless steel, tantalum, niobium, or zirconium may be used.

One solution to achieving biocompatibility, hermeticity, and galvanic and electrolytic compatibility for an implanted device is to encase the device in a protective environment. It is well known to encase implantable devices with glass or with a case of ceramic or metal. Schulman, et al. (U.S. Pat. No. 5,750,926) is one example of this technique. It is also known to use alumina as a case material for an implanted device as disclosed in U.S. Pat. No. 4,991,582. These cases are often too thick for use with miniature implantable devices, such as the prosthetic retinal implants of Second Sight, LLP. The case unacceptably increases the size of the device and becomes a limiting factor as to where the devices may be placed in the body.

It is also known to protect an implantable device with a thin layer or layers of an electrically insulating, protective material, as disclosed by Schulman, et al. (U.S. Pat. No. 6,043,437). Coatings of alumina, zirconia, or other ceramic, less than 25 microns thick, were applied by evaporative coating, vapor deposition, or ion-beam deposition.

Disadvantageously, the sensor described in the referenced patent and patent applications is relatively thick. For some applications, where small size is required, such as when a device is placed in an eye, eyelid, or in a fingertip, space is very limited and only a very small device will fit. There remains a need for yet a smaller sensor or a stimulator that performs all of the same functions as the prior apparatus, i.e., that provides working electrodes exposed to living tissue, perhaps with a selected enzyme placed over one electrode, and with hermetically-sealed electronic circuitry controlling the stimulator or sensor and communicating with other internal or external devices. The present invention advantageously addresses these and other needs.

U.S. Pat. No. 5,660,163 discloses an implantable glucose sensor that is fabricated on a ceramic substrate. Working electrodes and other elements associated with the sensor are exposed to a conductive fluid contained within a reservoir or inner sheath that covers the substrate. An outer sheath is also placed over the sensor, with a window formed over one of the working electrodes. A selected enzyme, such as glucose oxidate, is placed within the window. As disclosed in U.S. Pat. No. 5,660,163, five wires or conductors are attached to the electrodes and connected to electronic circuitry, e.g., a circuit such as is shown in FIG. 3 of the '163. U.S. Pat. No. 5,660,163 is incorporated herein by reference.

Additional features, aspects, and improvements of a glucose sensor of the type disclosed in U.S. Pat. No. 5,660,163 are further disclosed in U.S. Pat. No. 6,081,736; U.S. Pat. No. 6,119,028; and 5,999,848; each of which above-referenced patent applications is incorporated herein by reference.

SUMMARY OF THE INVENTION

The implantable biocompatible device of the instant invention is coated with a thin film of ultra-nanocrystalline diamond. The device is generally an integrated circuit chip that contains electronic circuitry for communicating with living tissue. The biocompatible device may be either an implanted stimulator or a sensor of living tissue function. An ultra-nanocrystalline diamond thin film coating assures that the device will be biocompatible and hermetically sealed. Ultra-nanocrystalline diamond may be patterned by conventional methods, including photolithography, seeding, and oxygen etching, to expose electrodes to the living tissue. Further, the ultra-nanocrystalline diamond may be doped, by a variety of known methods, to create an electrically conductive area that acts as an electrode, which may in turn contact living tissue to be a stimulator or a sensor. The ultra-nanocrystalline diamond coating provides a conformal coating on the biocompatible device, which is of approximately uniform thickness around sharp corners and on high aspect-ratio parts. The conformal nature of the coating helps assure hermeticity and strength despite the presence of difficult to coat shapes.

OBJECTS OF THE INVENTION

It is an object of the invention to provide an ultra-nanocrystalline diamond coated device that is hermetically sealed and biocompatible for implantation in a living body.

It is an object of the invention to provide an ultra-nanocrystalline diamond coated device that is has a uniform thickness coating around corners such that the coating maintains its hermetic sealing capability.

It is an object of the invention to provide an electrically insulating ultra-nanocrystalline diamond coated integrated circuit wherein the coating is patternable via conventional techniques to reveal electrodes.

It is an object of the invention to provide an ultra-nanocrystalline diamond coated integrated circuit wherein the coating contains openings to reveal electrodes.

It is an object of the invention to provide an electrically insulating ultra-nanocrystalline diamond coated integrated circuit wherein the coating is patterned by selective doping to yield integral electrodes.

It is an object of the invention to provide an implantable device, including electrodes and electronic circuitry that does not require a lid or cover for hermetically sealing hybrid electronic circuitry.

Other objects, advantages and novel features of the present invention will become apparent from the following detailed description of the invention when considered in conjunction with the accompanying drawing.

DETAILED DESCRIPTION OF THE PREFERRED EMBODIMENTS

Figure 1:
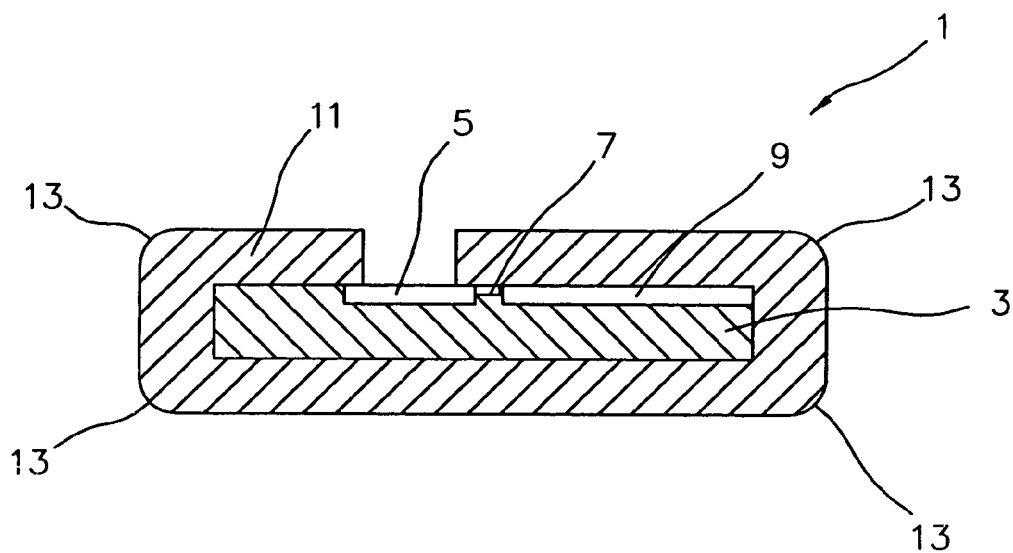
FIG. 1 illustrates a cross-sectional view of the integrated circuit coated with ultra-nanocrystalline diamond.

Ultra-nanocrystalline diamond (UNCD) thin film coatings exhibit excellent mechanical, electrical, and electrochemical properties. Using a thin film coating deposition process, such as that disclosed by Gruen and Krauss (U.S. Pat. No. 5,772,760), yields a coating that is inherently low in porosity, electrically nonconductive and biocompatible. Coatings as thin as 40 nm have demonstrated excellent hermetic properties. UNCD thin film coatings are conformal when applied to complex or high aspect-ratio shapes. Since UNCD can be either patterned or selectively deposited, it also permits exposure of conductors and/or vias for interconnection with other components.

Characteristics of this UNCD coating that make it particularly well suited to the present invention are:

uniform morphology resulting in a very high bulk density, highly conformal and able to cover very high-aspect ratio features uniformly, electrical properties can be controlled by varying the deposition parameters, so as to make selected areas electrically conductivity, low-temperature deposition thereby avoiding damage to electrical and passive components, and easily patternable via selective seeding, photolithography, or oxygen etching.

UNCD coating properties are not all present in any other single coating candidate for microchip packaging. Alternative coatings are conventional chemical vapor deposited diamond thin films, diamond-like carbon, or SiC. UNCD coatings exhibit:

(a) extremely low surface roughness (20–30 nm), approximately independent of film thickness up to approximately 10 μm thickness;

(b) extremely good conformality when deposited on high aspect-ratio features;

(c) extremely low coefficient of friction;

(d) high hardness, fracture toughness, flexural strength, and wear life, (e) low electrical conductivity, but can be doped to become conductive, and (f excellent resistant to degradation in living tissue environments.

The UNCD coating consists primarily of phase pure randomly oriented diamond crystallites. UNCD coatings are grown using a microwave plasma chemical vapor deposition technique involving a $C_{60}$/Ar or $CH_4$/Ar chemistry, which provides $C_2$ dimers as the main growth species that insert directly into the growing diamond lattice with a low energy barrier. The limited amount of atomic hydrogen in the plasma leads to a very high re-nucleation rate ($\sim 10^{11}$ cm$^{-2}$ sec$^{-1}$). This results in UNCD coatings with 2 to 5 nm grain size and 0.4 nm grain boundaries that provide the unique properties described herein. In addition, the low activation energy for $C_2$ species incorporation into the growing film yields UNCD films at temperatures as low as approximately 350° C. This temperature is very low compared to that required by many conventional coating processes, such as glass encapsulation or chemical vapor deposition.

The present invention uses the "chip" of an integrated circuit chip (which contains desired electronic circuitry) as the substrate for the stimulator or sensor, with the substrate and electronic circuitry being covered, as required, with a protective UNCD coating. Such approach advantageously eliminates the need for a hermetically sealed lid or cover, and thus allows the stimulator or sensor to be made much thinner than has heretofore been possible.

Integrated circuits that are implanted in a living body benefit from a UNCD coating that, in addition to biocompatibility, corrosion resistance, and hermeticity, can be patterned to expose the electrodes.

A UNCD protective coating covers the substrate, hermetically sealing the circuitry under the coating. Electrodes associated with the implantable device may be selectively left uncovered by the protective coating, thereby allowing such electrodes to be exposed to body tissue and fluids when the stimulator is implanted in living tissue. The exposed electrodes must be biocompatible. To this end, the electrodes may be plated with a biocompatible metal, such as platinum or iridium or alloys of platinum and/or iridium.

Alternately, using any of several patterning techniques that are well known in the art, it is possible to expose selected electrical contacts by selectively removing portions of the UNCD coating. There are several known permutations and combinations of process steps that can lead to this result.

Also, the UNCD coating itself may be selectively doped so as to create electrically conductive integral portions of the coating that then act as electrodes, which in turn contact the living tissue.

The inert nature of a very thin coating of UNCD was demonstrated by the present inventors. A silicon substrate coated with 40 nm of UNCD film was exposed to silicon etchant having a composition of 67% $HNO_3$ and 33% HF, by volume. The etchant was placed drop-wise on the UNCD film, where it was allowed to stand at 60° C. for one-hour. The coating had been unaffected when observed microscopically at 1000× after this exposure.

Therefore, the UNCD film coating may be used as part of a hermetic chip level packaging process to isolate implantable electronic and passive components from chemical or electrolytic attack in the body.

The UNCD coating on an integrated circuit is "conformal", which means that the coating has a uniform thickness as the coating follows the contours of the device. Achieving a conformal coating on high aspect-ratio parts and around sharp corners on these devices is a particular challenge for thin films that are deposited by other means.

In accordance with another aspect of the invention, an efficient integral capacitor may be formed between the stimulator and the living tissue by virtue of depositing a very thin layer of UNCD insulating film on the surface of the stimulator such that the thin film causes a capacitor to be formed. Such a capacitor can advantageously be used to effectively stop current flow to the living tissue, thereby avoiding harm to the tissue that is caused by electrical current flow, while allowing the stimulating voltage signal to pass to the tissue.

The invention may further be characterized as a method of making an implantable device that is either a stimulator or a sensor, where the device includes a substrate, electrodes formed on the substrate, and electrical circuitry formed on the substrate. Such method includes the steps of: (a) forming the electrical circuitry on the surface of a semiconductor substrate; (b) forming electrodes on the semiconductor substrate; (c) electrically interconnecting the electrodes with the electrical circuitry through the use of conductive paths that pass through or on the body of the semiconductor substrate; and (d) depositing a protective coating of UNCD over the entire surface area of the substrate, except for select areas of the electrodes, so that all but the exposed area of the electrodes is sealed and protected.

FIG. 1 provides a cross-sectional view of a preferred embodiment of a coated integrated circuit 1. Due to the extremely thin film that is required, these figures are not drawn to scale. The integrated circuit is shown, where the silicon substrate 3 contains an electrode 5 on one surface that is connected by metal trace 7 to active circuitry 9. The silicon substrate 3 is coated with an ultra-nanocrystalline diamond 11. The ultra-nanocrystalline diamond 11 coating has been removed in a selected portion to expose electrode 5 such that electrode 5 can contact living tissue directly when implanted. The ultra-nanocrystalline diamond 11 has an approximately uniform thickness and has rounded corners 13 which are formed as part of the normal application process. The rounded corners 13 are an advantage for implanted ultra-nanocrystalline diamond coated devices such as coated integrated circuit 1 because they eliminate sharp corners and sharp edges that might otherwise create stress concentrations in the living tissue which could damage the tissue.

Figure 2:
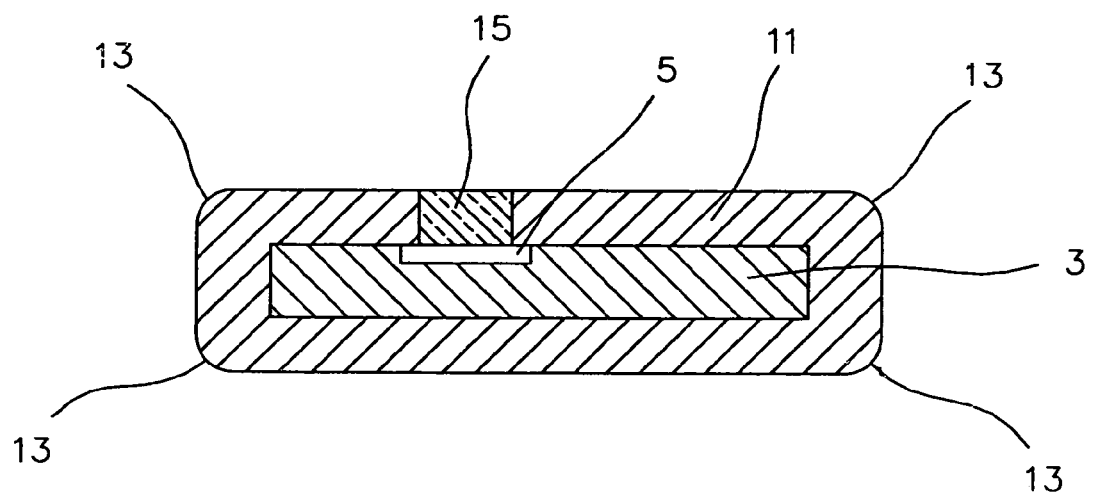
FIG. 2 depicts a cross-sectional view of an integrated circuit having a conductive portion of the ultra-nanocrystalline diamond coating.

FIG. 2 provides a cross-sectional view of an integrated circuit as in FIG. 1, however, the normally electrically insulating ultra-nanocrystalline diamond 11 has been doped in a selected area to provide electrically conductive doped ultra-nanocrystalline diamond electrode 15. This preferred configuration allows the ultra-nanocrystalline diamond 11 to be completely hermetically sealed around the silicon substrate 3, thereby protecting the silicon substrate 3 and electrodes 5 from exposure to living tissue.

Obviously, many modifications and variations of the present invention are possible in light of the above teachings. It is therefore to be understood that, within the scope of the appended claims, the invention may be practiced otherwise than as specifically described.

What is claimed is:

1. A biocompatible device which communicates electrical signals with tissue in a living body, comprising:
   an integrated circuit, said integrated circuit comprising a semiconductor substrate having at least one surface on which electronic circuitry is formed;
   electrodes for contacting the living tissue which are formed on said at least one surface of said semiconductor substrate;
   means for electrically connecting said stimulator electrodes with said electronic circuitry formed on said at least one surface of said semiconductor substrate;
   an ultra-nanocrystalline diamond coating that covers all areas of said at least one surface of said semiconductor substrate, except for selected portions of said stimulator electrodes; and
   means for making electrical connection with and providing operating power to said electronic circuitry formed on said at least one surface of said semiconductor substrate.

2. The biocompatible device according to claim 1 wherein said integrated circuit comprises a sensor.

3. The biocompatible device according to claim 1 wherein said integrated circuit comprises a stimulator.

4. The biocompatible device according to claim 1 wherein said ultra-nanocrystalline diamond coating is approximately constant in thickness over uneven portions of said device to provide a smooth coating with rounded edges.

5. The biocompatible device according to claim 1 wherein said ultra-nanocrystalline diamond coating is patterned by photolithography.

6. The biocompatible device according to claim 1 wherein said ultra-nanocrystalline diamond coating is patterned by selective seeding.

7. The biocompatible device according to claim 1 wherein said ultra-nanocrystalline diamond coating is patterned by oxygen etching.

8. A biocompatible device which communicates electrical signals with tissue in a living body, comprising:
   an integrated circuit, said integrated circuit comprising a semiconductor substrate having at least one surface on which electronic circuitry is formed;
   electrodes for contacting the living tissue which are formed on said at least one surface of said semiconductor substrate;
   means for electrically connecting said stimulator electrodes with said electronic circuitry formed on said at least one surface of said semiconductor substrate;
   a diamond coating that covers all areas of said at least one surface of said semiconductor substrate, except for selected portions of said stimulator electrodes; and
   means for making electrical connection with and providing operating power to said electronic circuitry formed on said at least one surface of said semiconductor substrate.

* * * * *